United States Patent [19]

Afonso et al.

[11] Patent Number: 5,179,093
[45] Date of Patent: Jan. 12, 1993

[54] QUINOLINE-DIONES

[75] Inventors: Adriano Afonso, West Caldwell; Stuart W. McCombie, Caldwell; Jay Weinstein, Upper Montclair, all of N.J.

[73] Assignee: Schering Corporation, Kenilworth, N.J.

[21] Appl. No.: 698,204

[22] Filed: May 10, 1991

[51] Int. Cl.$^5$ .......................... C07D 215/22
[52] U.S. Cl. .................. 514/235.2; 514/43; 514/243; 514/248; 514/249; 514/258; 514/259; 514/295; 514/300; 514/301; 514/302; 514/303; 514/312; 514/367; 514/375; 514/387; 514/405; 514/412; 514/443; 514/456; 544/128; 544/184; 544/236; 544/350; 546/114; 546/116; 546/118; 546/119; 546/122; 546/155; 536/53; 548/153; 548/218; 548/453; 548/311.4; 548/364.4; 548/311.7; 548/303.1; 548/360.5; 549/23; 549/287

[58] Field of Search .................. 514/312, 235.2; 546/155; 544/128

[56] References Cited

U.S. PATENT DOCUMENTS

| | | | |
|---|---|---|---|
| 3,025,299 | 3/1962 | Pfister et al. | 546/155 |
| 3,132,140 | 5/1964 | Jaffe | 546/155 |
| 3,449,335 | 6/1969 | Copeland | 546/155 |
| 3,715,360 | 2/1973 | Gaeng et al. | 546/155 |
| 3,960,868 | 6/1976 | Ferrini et al. | 546/155 |
| 3,962,445 | 6/1976 | Buckle | 546/155 |
| 4,006,237 | 2/1977 | Buckle et al. | 546/155 |
| 4,022,770 | 5/1977 | L'Eplattenier | 546/155 |
| 4,031,099 | 6/1977 | Buckle et al. | 546/156 |
| 4,107,310 | 8/1978 | Allais et al. | 546/155 |
| 4,124,587 | 11/1978 | Hardtmann | 546/155 |
| 4,168,312 | 9/1979 | Schact et al. | 546/155 |
| 4,187,309 | 2/1980 | Hardtmann | 546/156 |
| 4,190,659 | 2/1980 | Hardtmann | 546/155 |
| 4,526,894 | 7/1985 | Enomoto | 546/155 |
| 4,607,039 | 8/1986 | Le Count et al. | 546/155 |
| 4,902,693 | 2/1990 | Blythin | 546/155 |
| 4,959,363 | 9/1990 | Wentland | 546/155 |

FOREIGN PATENT DOCUMENTS

| | | |
|---|---|---|
| 93251 | 11/1983 | European Pat. Off. |
| 385630 | 9/1990 | European Pat. Off. ............ 546/153 |
| 269382 | 6/1989 | German Democratic Rep. |
| 44-16373 | 7/1969 | Japan .................... 546/155 |
| 63-295561 | 12/1988 | Japan . |
| 2-152966 | 6/1990 | Japan . |

OTHER PUBLICATIONS

Wolfbeis et al. Monatsch. vol. III pp. 93-112 (1980).
Trathnigg et al. Monatsch. vol. 115 pp. 1353-1368 (1984).
Clark et al. J. Chem. Soc. (London) 1964 pp. 438-445.
Knierzinger et al. J. Het. Chem vol. 17 pp. 225-229 (1980).
Wolfbeis et al XII, Z. Naturforsch vol. 32b pp. 1077-1083 (1977).
Wolfbeis et al VI, Z. Naturforsch vol. 31b, pp. 514-519 (1976).
Trathnigg et al. Chem. Abstr. vol. 102 entry 1318676n (1984).
Wolfbeis et al. Chem. Abstr vol. 93 entry 73744a (1980).
Yoshizaki et al, CA 113: 211864Z.
Schaefer et al, CA 109: 170249Z abstracting East German 242806.
Derwent Abstract J 9005-752B.
Derwent Abstract J8 9035-827-B.

Primary Examiner—Donald G. Daus
Attorney, Agent, or Firm—Eric S. Dicker; John J. Maitner; Matthew Boxer

[57] ABSTRACT

Compounds of the formula

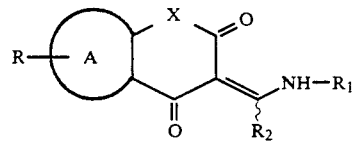

or a pharmaceutically acceptable salt thereof wherein,
R is H, halogen, ($C_1$-$C_6$) alkyl, N($C_1$-$C_6$ alkyl/aryl)$_2$, OH, O—($C_1$-$C_6$) alkyl/aryl, $CH_2OH$, COOH, COO-alkyl/aryl, $SO_2NH_2$, or $SO_2NH$ ($C_1$-$C_6$ alkyl/aryl);
$R_1$ is $C_1$-$C_6$ alkyl, cycloalkyl, $C_2$-$C_6$ alkenyl, heteroaryl, substituted heteroaryl, heterocycloalkyl, —$CH_2$-aryl, —$CH_2$-substituted aryl, —$CH_2$-heteroaryl, or —$CH_2$-substituted heteroaryl;
$R_2$ is H, $C_1$-$C_6$ alkyl or aryl;

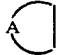

is an aromatic ring or a heteroaromatic ring; and
X is O or N-(alkyl/aryl/alkyl-aryl/alkoxylalkoxyaryl)
are described. These compounds are useful as agents for treating viruses.

12 Claims, No Drawings

QUINOLINE-DIONES

BACKGROUND

This invention relates to compounds having antiviral activity, pharmaceutical compositions thereof, and methods of treatment utilizing the compositions. In particular, this invention is related to compounds having antiviral activity against herpes group viruses, pharmaceutical compositions containing the compounds, and methods of treating herpes group viruses using the pharmaceutical compositions.

There are four separate herpes group viruses which infect and cause disease in humans. These are (1) herpes simplex virus 1 and 2 (HSV-1 and HSV-2, respectively); (2) cytomegalovirus (CMV); (3) varicella-zoster virus (VZ); and (4) Epstein-Barr virus (EB). Examples of diseases associated with herpes simplex virus infection include herpes labialis, genital herpes (herpes progenitalis), neonatal herpes, herpetic keratitis, eczema herpecticum, disseminated herpes, occupational herpes, herpectic gingivostomatitis, meningitis (aseptic), and encephalitis.

VZ virus is associated with chicken-pox (varicella) and shingles (zoster) in humans.

CMV is wide spread in humans and numerous other mammals. A great majority of human CMV infections are subclinical; that is, the primary infection occurs with no signs or symptoms. An exception to this is a congenital infection which occasionally gives rise to cytomegalic inclusion body disease in infants. There is also a mononucleosis-like syndrome caused by the virus.

A great majority of serious cases due to CMV infection comes from recurring infections in immuno-compromised individuals, such as in transplant patients and in cancer patients. It has been estimated that silent CMV infections have occurred in a majority of humans by the time adulthood is reached.

Examples of drugs used to treat herpes infections include: (1) IUDR (5'-iodo-2'-deoxyuridine); (2) Ara-C (1-[beta-D-arabinofuranosyl]-cytosine); (3) Ara-A (9-beta-D-arabinofuranosyladenine); and (4) Acyclovir(9-[(2-hydroxyethoxy)methyl]guanine). Also Haines et al. (U.S. Pat. No. 4,757,088 issued Jul. 12, 1988) discloses that lidocaine (2-(diethylamino)-N-(2,6-dimethylphenyl)acetamide) is an antiviral agent in cell culture against HSV-1 and HSV-2, and is able to treat herpes virus infections of mammals. Haines et al. also disclose that lidocaine is particularly effective in the treatment of HSV oral and genital lesions in humans. According to Haines et al., the addition of pantothenic acid or its alcohol and salt forms, dexpanthenol and pantothenate respectively, to lidocaine or lidocaine hydrochloride significantly enhances the antiviral activity of those drugs.

In view of current interest in the art for finding useful antiviral agents, in particular, useful agents against herpes group viruses, any new compounds exhibiting antiviral activity would be a welcome contribution to the art. This invention provides such a contribution.

SUMMARY OF THE INVENTION

This invention provides compounds which are useful as antiviral agents against DNA containing viruses such as herpes group viruses. In particular, the compounds of this invention are useful against HSV-1 and HSV-2 and may also prove useful against CMV and EB.

The compounds of this invention are advantageous over known compounds because they inhibit early events in the viral replication.

The invention relates to compounds of the formula

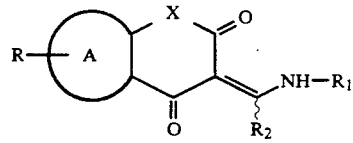

or a pharmaceutically acceptable salt thereof wherein,

R is H, halogen, ($C_1$–$C_6$) alkyl, N($C_1$–$C_6$ alkyl/aryl)$_2$, OH, O—($C_1$–$C_6$) alkyl/aryl, $CH_2OH$, COOH, COO—alkyl/aryl, $SO_2NH_2$, or $SO_2NH$ ($C_1$–$C_6$ alkyl/aryl);

$R_1$ is $C_1$–$C_6$ alkyl, cycloalkyl, $C_2$–$C_6$ alkenyl, heteroaryl, substituted heteroaryl, heterocycloalkyl, —$CH_2$—aryl, —$CH_2$—substituted aryl, —$CH_2$—heteroaryl, or —$CH_2$—substituted heteroaryl;

$R_2$ is H, $C_1$–$C_6$ alkyl or aryl;

is an aromatic ring or a heteroaromatic ring; and
X is O or N-(alkyl/aryl/alkyl-aryl/alkoxylalkoxyaryl).

Preferred are compounds of formula I wherein X is N-(alkyl/aryl/alky-aryl).

Among these, more preferred are compounds of formula I wherein X is selected from the group consisting of N-benzyl, N-hexyl, and N-heptyl.

Also preferred are compounds of formula I wherein

is an aromatic ring, especially phenyl.

Also preferred are compounds of formula I wherein $R_2$ is H.

Also preferred are compounds of formula I wherein $R_1$ is $CH_2$—aryl, or —$CH_2$—heteroaryl, especially benzyl or $CH_2$—pyridyl.

Also preferred are compounds of formula I wherein R is H halogen, or $C_1$–$C_6$ alkyl. In particular, compounds of formula I wherein R is $CH_3$, Cl, or H are preferred. Compounds of formula I wherein R is H are especially preferred.

Also preferred are compounds of formula I wherein X is N-(alkyl/aryl/alky-aryl),

is an aromatic ring, R is H, Cl, or methyl; $R_2$ is H, and $R_1$ is benzyl, or —$CH_2$—pyridyl.

The invention also relates to compounds of the formula

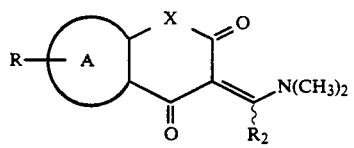
IV or a pharmaceutically acceptable salt thereof wherein,

R is H, halogen, ($C_1$-$C_6$) alkyl, N($C_1$-$C_6$ alkyl/aryl)$_2$, OH, O—($C_1$-$C_6$) alkyl/aryl, $CH_2OH$, COOH, COO—alkyl/aryl, $SO_2NH_2$, or $SO_2NH$ ($C_1$-$C_6$ alkyl/aryl);

$R_2$ is H, $C_1$-$C_6$ alkyl or aryl;

is an aromatic ring or a heteroaromatic ring; and

X is O or N-(alkyl/aryl/alkyl-aryl/alkoxylalkoxyaryl).

Exemplary compounds of formula I of the invention include:

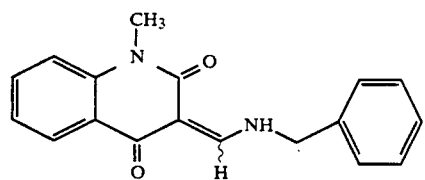

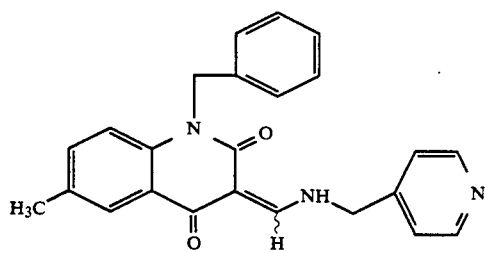

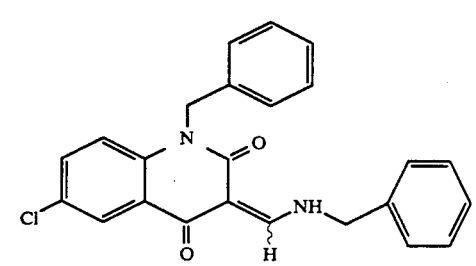

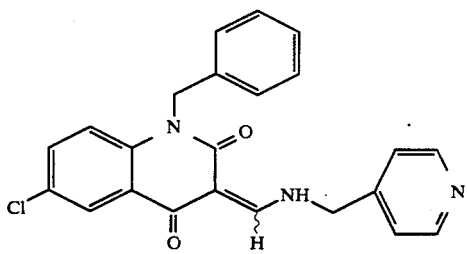

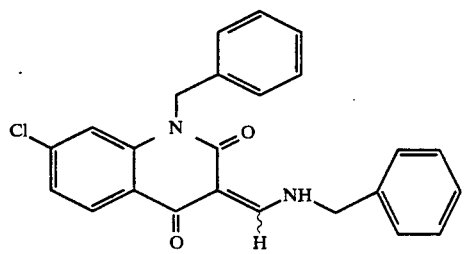

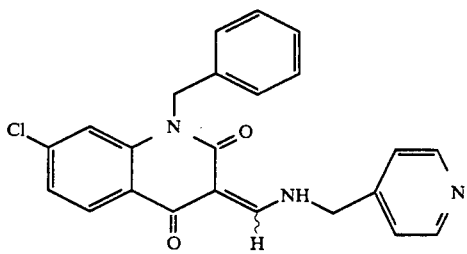

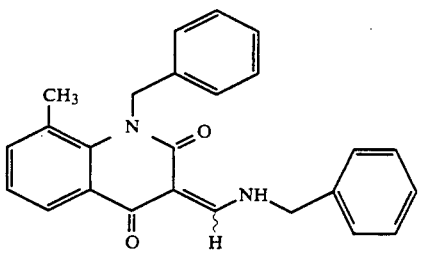

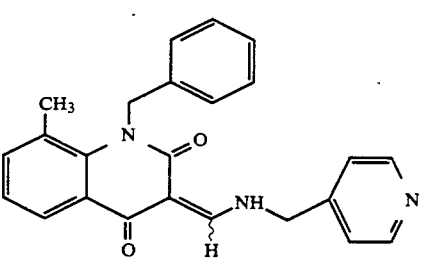

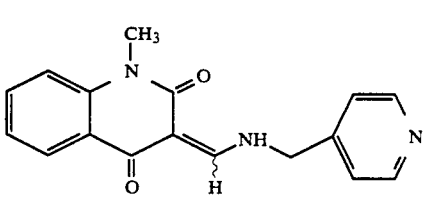

-continued
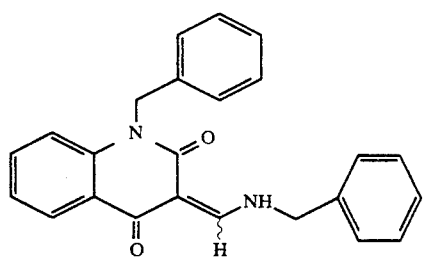
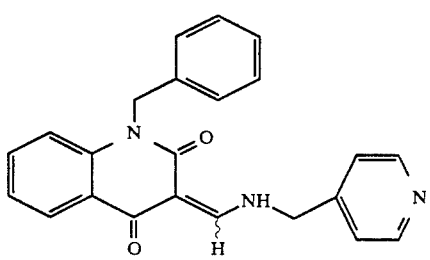
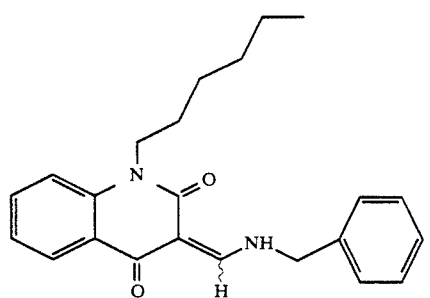
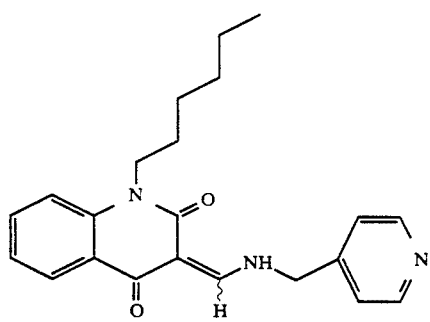
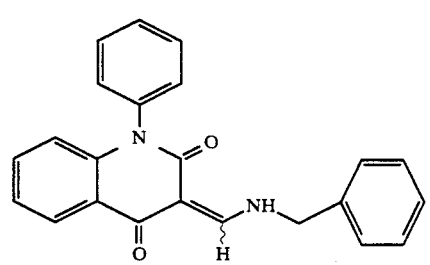
-continued
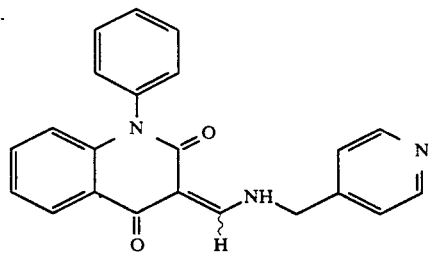
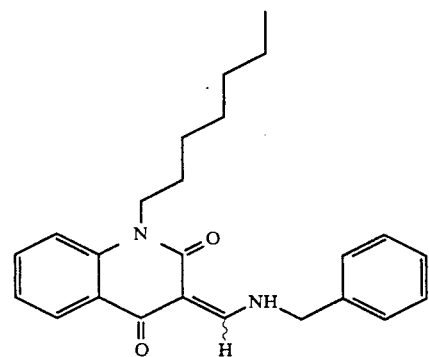
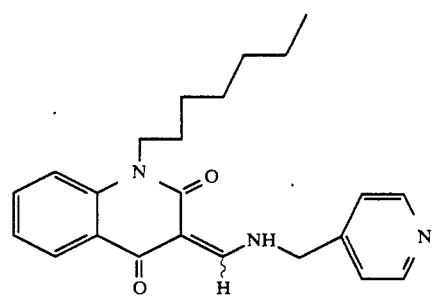
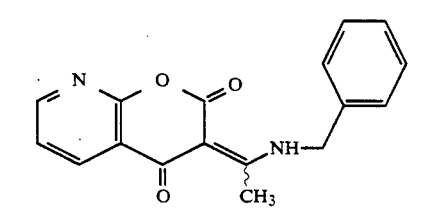
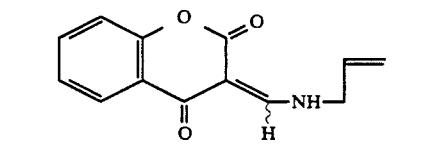
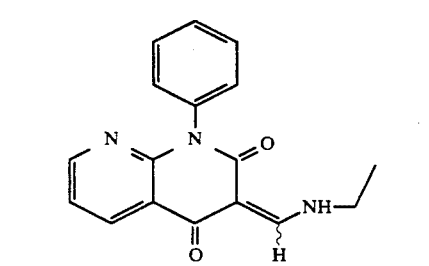

-continued
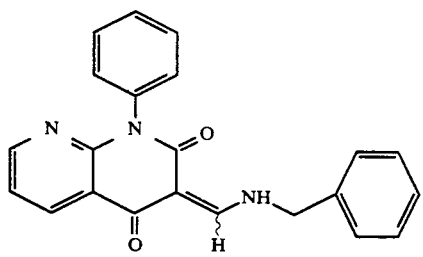
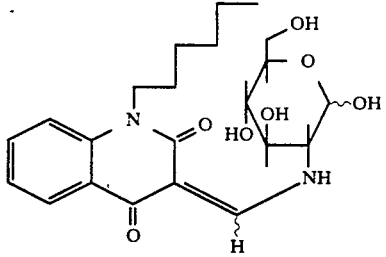
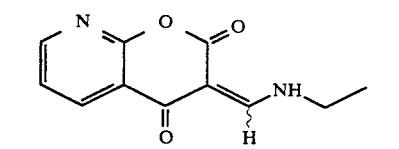
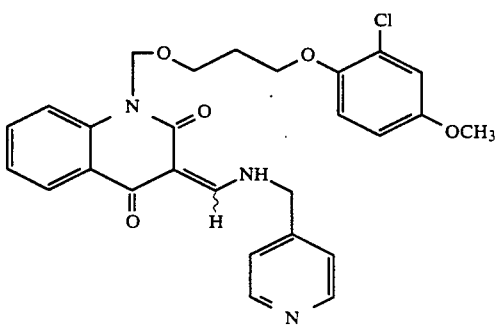
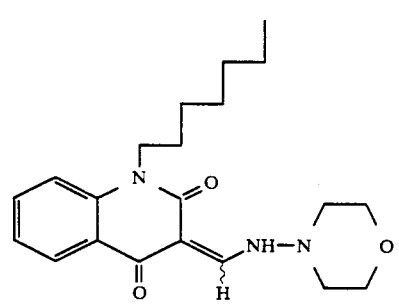
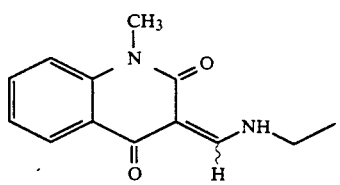
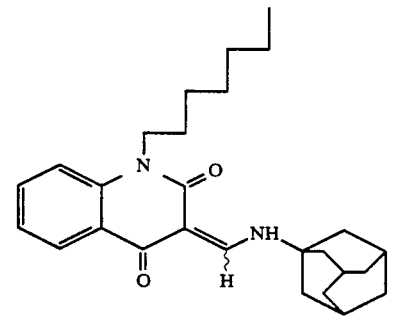
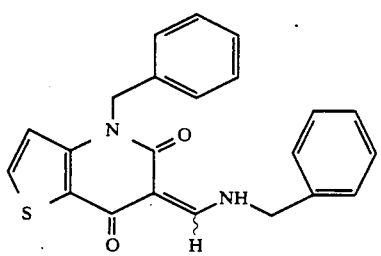
and
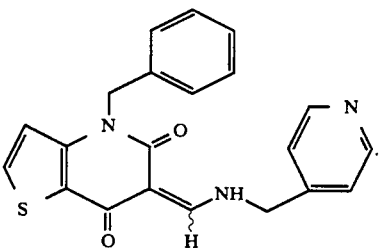
Among these compounds, the following are especially preferred:
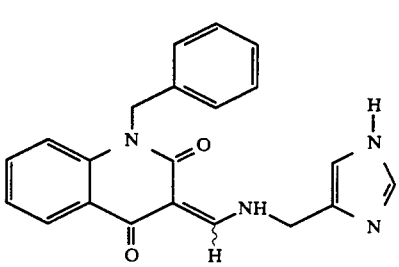

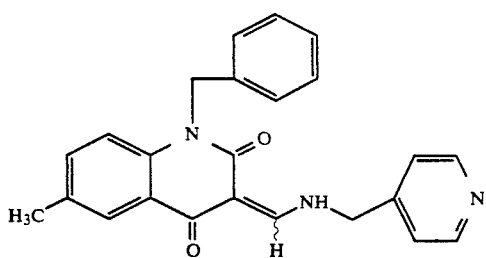

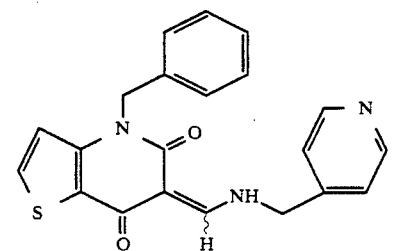

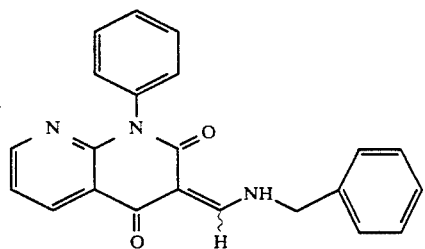

and

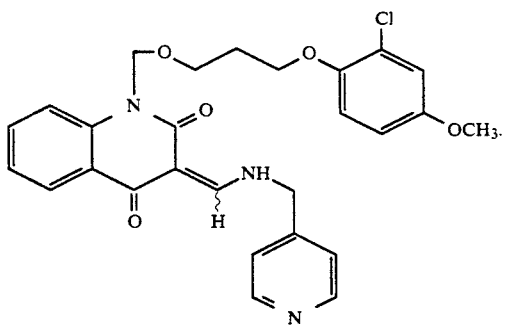

The most preferred compound of the invention is

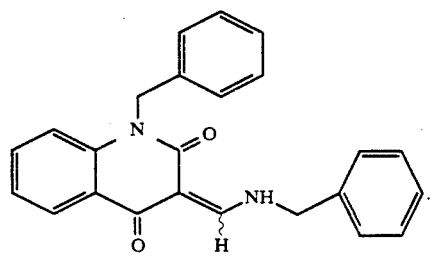

Exemplary compounds of formula IV of the invention include:

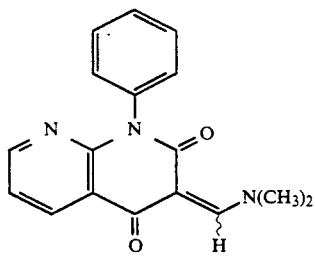

and

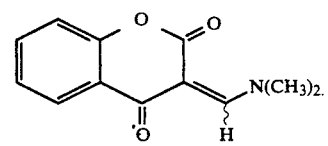

The invention also relates to pharmaceutical compositions comprising a compound of formula I in combination with a pharmaceutically acceptable carrier.

The invention also relates to pharmaceutical compositions comprising a compound of formula IV in combination with a pharmaceutically acceptable carrier.

The invention also relates to a method for treating a viral infection which comprises administering to a mammal in need of such treatment an effective amount of a compound of formula I for such purpose.

The invention also relates to a method for treating a viral infection which comprises administering to a mammal in need of such treatment an effective amount of a compound of formula IV for such purpose.

DETAILED DESCRIPTION OF THE INVENTION

When used herein, the terms listed below have the scope indicated, unless indicated otherwise.

Alkyl—represents straight or branched hydrocarbon chains, which contain from 1 to 7 carbon atoms. Representative examples include methyl, ethyl, propyl and the like. Alternatively, the number of carbon atoms in a particular alkyl may be specified. For example, $C_1$-$C_6$ alkyl refers to an alkyl which may have one to six carbon atoms.

Alkenyl—represents straight or branched hydrocarbon chains, which contain from 2 to 7 carbon atoms, and having at least one carbon to carbon double bond. Up to three carbon to carbon double bonds may be present when seven carbon atoms are in alkenyl. Preferably, one to two carbon to carbon double bonds are present in alkenyl. Representative examples of alkenyl include vinyl, allyl, butenyl, and the like. Alternatively, the number of carbon atoms in a particular alkenyl may be specified. For example, $C_2$-$C_6$ alkenyl refers to an alkenyl which, may have two to six carbon atoms. Representative examples include methyl, ethyl, propyl and the like.

Alkoxy—represents —O—alkyl wherein alkyl is as defined above.

Alkoxyalkoxyaryl—represents a group wherein an alkyl group is joined through an oxygen atom to another alkyl group which in turn is joined through an oxygen atom to an aryl group wherein the point of attachment to the alkyl group is at a ring carbon. Alkyl is defined as above and aryl is defined as below. The aryl group may contain additional sustituents selected from the group consisting of halogen atoms, alkoxy, alkyl and amino. Representive examples of alkoxyalkoxyaryl include phenoxypropyloxymethyl, phenoxyethyloxymethyl, and (chloro-methoxy)propyloxymethyl.

Aryl (including the aryl portion of —CH$_2$-aryl-)—represents a mono or bi-cyclic aromatic system. Examples of preferred aryl groups include those having from 6 to 14 carbon atoms. Representative examples include phenyl, 1-naphthyl, 2-naphthyl and indanyl. The aryl group may contain additional substituents selected from the group consisting of: halogen atoms (e.g., Cl, Br, F, and/or I), alkoxy, alkyl, and amino.

Alkyl-aryl—represents alkyl as defined herein, with one or more of its hydrogens replaced by aryl as defined herein.

Cycloalkyl—represents a hydrocarbon ring system having a cyclic or polycyclic structure and having from 5 to 10 carbon atoms. Representative examples include cyclopentyl, cyclohexyl, cycloheptyl, and adamantyl.

Haloalkyl—represents alkyl as defined herein, with one or more of its hydrogens replaced by halogen as defined herein.

Heteroaryl (including the heteroaryl portion of —CH$_2$-heteroaryl)—represents aromatic systems having at least one O, S and/or N heteroatom in the ring structure. Examples of preferred heteroaryl groups include those containing from 3 to 14 carbon atoms. Representative examples of heteroaryl groups include but are not limited to: 2-, 3- or 4-pyridyl, 2- or 3-furyl, 2- or 3-thienyl, 2-, 4- or 5-thiazolyl, 2-, 4- or 5-imidazolyl, 2-, 4-or 5-pyrimidinyl, 2-pyrazinyl, 3- or 4-pyridazinyl, 3-, 5- or 6-[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, 2- or 3-pyrrolyl, 2- or 3-N-methylpyrrolyl, and the like.

Heterocycloalkyl—represents a 5- or 6-membered cycloalkyl ring wherein at least one heteroatom is part of the ring. Representative examples of heterocycloalkyl groups include morpholino, tetrahydrothiophenyl, piperidinyl, piperazinyl, pyrollidinyl, imidazolidinyl, and tetrahydropyranyl. Tetrahydropyranyl includes glucosyl, ribosyl, and the like.

Substituted aryl—represents an aryl group, as defined above, wherein one of more of the H atoms attached to the ring carbon atoms are replaced by groups independently selected from the group consisting of: halo, alkyl, OH, alkoxy, phenoxy, NH$_2$, N(H, alkyl), and N(alkyl)$_2$ wherein each alkyl is the same or different and is as defined above. Preferred substituted aryl groups are substituted phenyl groups.

Substituted heteroaryl—represents a heteroaryl group, as defined above, wherein one of more of the H atoms attached to the ring carbon atoms are replaced by groups independently selected from the group consisting of: halo, alkyl, OH, alkoxy, phenoxy, NH$_2$, N(H, alkyl), and N(alkyl)$_2$ wherein each alkyl is the same or different and is as defined above. Preferred substituted heteroaryl groups are substituted pyridyl groups.

Halogen (or halo)—represents Cl, Br, F, and I.

An aromatic ring—represents a mono or bi-cyclic aromatic system wherein only carbon atoms form the ring structure. Examples of preferred aryl groups include those having from 6 to 14 carbon atoms. Representative examples include phenyl, 1-naphthyl, 2-naphthyl and indanyl. The aryl group may contain additional substituents selected from the group consisting of: halogen atoms (e.g., Cl, Br, F, and/or I), alkoxy, alkyl, and amino.

A heteroaromatic ring—represents an aromatic system having at least one O, S and/or N heteroatom in the ring structure. Examples of preferred heteroaryl groups include those containing from 3 to 14 carbon atoms. Representative examples of heteroaryl groups include but are not limited to: 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, 2- or 3-pyrrolyl, 2- or 3-N-methylpyrrolyl, and the like.

Also as used herein, C(O) represents C=O.

N(C$_1$–C$_6$ alkyl/aryl)$_2$-represents either N(C$_1$–C$_6$ alkyl,alkyl); N(C$_1$–C$_6$ alkyl,aryl); or N(C$_1$–C$_6$ aryl,aryl) wherein each alkyl and aryl are the same or different and are as defined above. The "/" sign when used in other places in the specification has a similar meaning.

⁓⁓⁓ as used herein denotes a chemical bond whose stereochemistry is not specifically defined. For example,

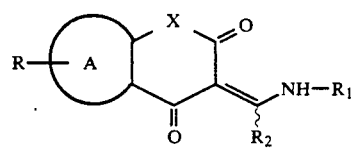

denotes compounds of the formula

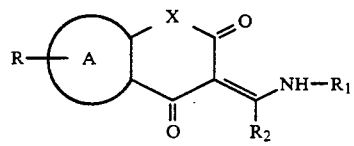

as well as compounds of the formula

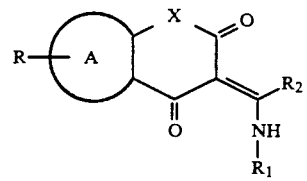

as well as mixtures thereof.

As can be seen, stereoisomers are possible about the double bond attached to the dicarbonyl ring. Just below are depicted two such possible stereoisomers:

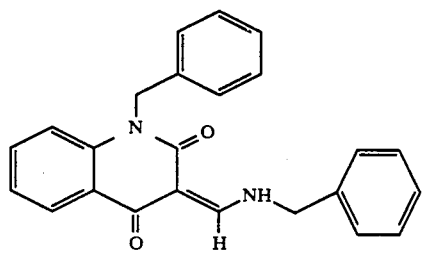

which is the "Z" isomer, and

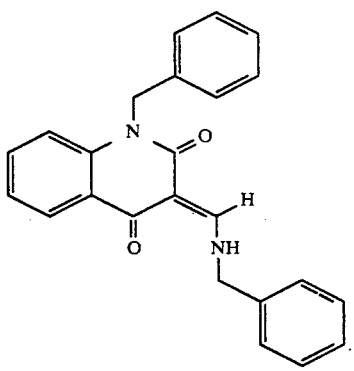

which is the "E" isomer.

A mixture of the E and Z isomers may be separated by conventional means such as high performance liquid chromatography.

Stereoisomers may also be possible elsewhere in the molecule.

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

The compounds of formula I may form carboxylic acid salts. Examples of such salts are the sodium, potassium, calcium, and aluminum salts. Also contemplated are salts formed with pharmaceutically acceptable amines such as ammonia, alkylamines, hydroxyalkylamines, N-methylglucamine and the like.

Certain compounds of the invention, e.g., those with a basic amine group, also form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ respectively from their respective salt forms in certain physical properties, such as solubility in polar solvents, but the salts are otherwise equivalent to their respective free bases for the purposes of this invention.

The compounds of formula I can be prepared by the processes described below. In these processes the substituents are as described below unless otherwise indicated. Those skilled in the art will appreciate that in the processes described below the reactions are carried out at a temperature high enough to allow the reaction to proceed at a reasonable rate, but not so high as to cause undue degradation of reactants and/or products. Those skilled in the art will appreciate that in the following reactions the desired products may be isolated by techniques well known in the art such as distillation, column chromatography, recrystallization, and the like.

The compounds of formula I of the invention may be prepared by the methods described below with reference to Formula Schemes 1 and 2 wherein R, $R_1$, $R_2$,

and X are as described above unless otherwise indicated.

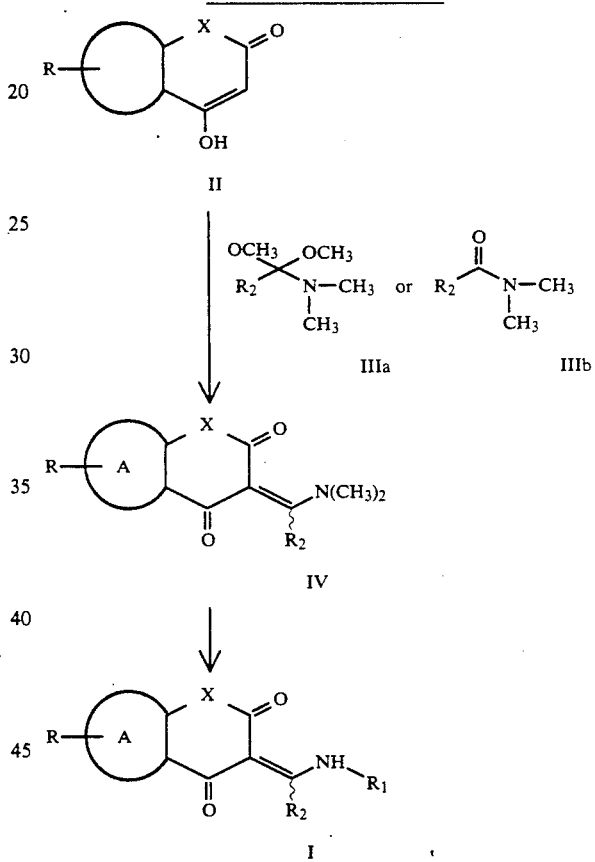

wherein R, $R_1$, $R_2$,

and X, are as described above.

More specifically, and as set forth in Formula Scheme 1, a compound of formula IV may be prepared by reacting a compound of formula II with a compound of formula IIIa in an organic solvent such as dichloromethane, tetrahydrofuran and the like at temperatures ranging from about room temperature to about 100° C. The resulting compound of formula IV may be purified by conventional techniques such as crystallization or column chromatography or it may be used directly in another synthetic step set forth in the present specification.

A compound of formula IV may also be prepared by reacting a compound of formula II with a dimethyl sulfate adduct of a compound of formula IIIb in a haloalkyl solvent such as dichloromethane, dichloroethane, and the like in the presence of an organic base such as di-isopropylamine, triethylamine, and the like, at temperatures ranging from about room temperature to about 80° C.

A compound of formula IV may be reacted with the appropriate amine, $R_1NH_2$, where $R_1$ is as described above in a polar organic solvent such as methanol, dichloromethane, tetrahydrofuran, and the like at a temperature in the range of about room temperature to about 90° C. to obtain a compound of formula I wherein R, $R_1$, $R_2$, and X, are as described above.

Compounds of formula I may also be prepared by methods analogous to those set forth in the literature e.g. Monatshefte fur Chemie 115, 1353–1368 (1984) Trathnigg et al and J. Heterocyclic Chem., 17, 225 (1980) Knierzinger et al which are hereby incorporated by reference.

Compounds of formula II are known or may be prepared by known methods.

Compounds of formula III are known or may be prepared in accordance with known methods.

FORMULA SCHEME 2

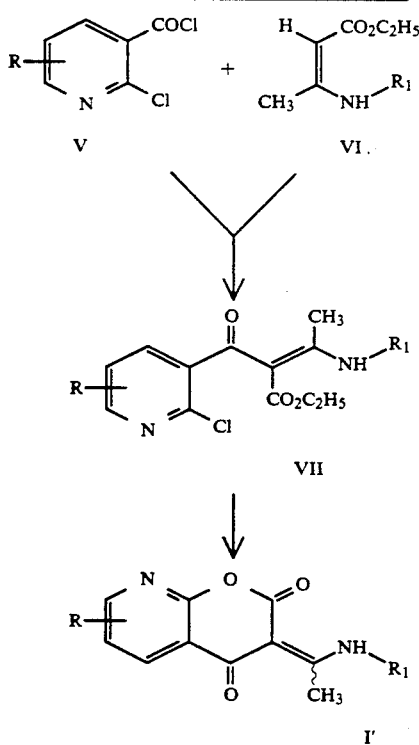

wherein R and $R_1$ are as described above.

In accordance with Formula Scheme 2, there is provided a synthetic route for preparing compounds of formula I' which are compounds of formula I wherein is a pyridyl nucleus, X is O and $R_2$ is $CH_3$. These compounds are prepared by reacting the appropriate pyridyl compound of formula V with an enamine of formula VI in a polar organic solvent such as dichloromethane, tetrahydrofuran and the like in the presence of an organic base such as triethylamine, diisopropylamine, di-isopropylethylamine and the like, to obtain a compound of formula VII. The reaction may be run at a temperature in the range of about 25° C. to about 100° C., preferably at about room temperature. The resulting compound of formula VII may be purified by conventional techniques such as crystallization or column chromatography or it may be used directly in another synthetic step set forth in the present specification.

The resulting compound of formula VII is then treated with a strong acid such as an organic acid like p-toluenesulfonic acid or, more preferably, methane sulfonic acid; or a strong mineral acid such as $H_2SO_4$, or, more preferably, hydrochloric acid; in an organic solvent such as tetrahydrofuran, dichloromethane, or more preferably 1,2-dichloroethane. The reaction is conducted at a temperature in the range of about 50° to about 100° C. or more preferably at the reflux temperature of the solvent being employed to afford a compound of formula I'. The resulting compound of formula I' may be purified by conventional techniques such as crystallization or column chromatography or it may be used directly in another synthetic step set forth in the present specification.

Starting materials of formulas V and VI are known or may be prepared in accordance with known methods.

The compounds of formula I of the invention are useful as agents for treating viruses. The compounds of formula IV of the invention are also useful as agents for treating viruses:

The anti-viral activity of the compounds of formula I and formula IV of the invention may be demonstrated in the protocols set forth below.

The compounds of this invention can be administered in any number of conventional dosage forms, e.g., topical, oral, parenteral, rectal, transdermal, inhalation and the like. Oral or rectal dosage forms include capsules, tablets, pills, powders, cachets, and suppositories. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, perfumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical, dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

The compounds of this invention may be administered by any conventional mode of administration by employing an antiviral effective amount of a compound of this invention for such mode. The dosages may be varied depending upon the requirements of the patient in the judgement of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 5 to about 100 mg/kg of body weight per day may be administered to provide antiviral activity. For example, when administered orally doses of from about 20 to about 60 mg/kg of body weight may be used; and when administered parenterally, e.g., intravenously, dosages of from about 5 to about 20 mg/kg body weight may be used.

When administered topically, the amount of compound administered varies widely with the amount of skin being treated, as well as with the concentration of active ingredient applied to the affected area. Preferably, topical compositions contain from about 0.10 to about 10 percent by weight of the active ingredient and are applied as needed according to the judgement of the attending clinician. When administered rectally, the compounds of this invention may be administered in daily doses rangling from about 0.1 mg/kg to abut 100 mg/kg of body weight.

The dosage to be administered and the route of administration depends upon the particular compound used, the age and general health of the patient and the severity of the viral condition. Thus, the dose ultimately decided upon must be left to the judgement of a trained health-care practitioner.

EXAMPLES

PREPARATION A

Preparation of 1-Benzyl-4-Hydroxy-6-Methyl-2(1H)-Quinolinone

Example 1

6-Methyl-Isatoic Anhydride

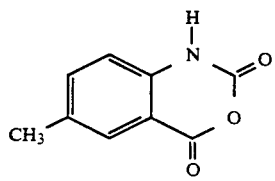

A solution of 2-amino-5-methyl-benzoic acid (4.5 gm) in 2N HCl (15 ml) and water (35 ml) was stirred vigorously while adding dropwise trichloromethyl chloroformate (5.6 gm). The reaction was stirred for an additional 10 minutes and then filtered; the solid cake was washed with water and dried under reduced pressure to afford the title compound as a light yellow powder (4.7 gm).

EXAMPLE 2

1-Benzyl-6-Methyl-Isatoic Anhydride

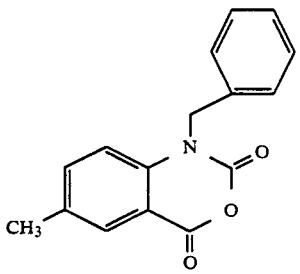

A solution of 6-methyl-isatoic anhydride (4.5 gm) in DMF (30 ml) was added dropwise to a stirred suspension of 60% sodium hydride (1.0 gm) in DMF (20 ml) under nitrogen atmosphere. The reaction was then warmed to 45° and stirred until hydrogen evolution ceased. It was then cooled and a solution of benzyl bromide (4.4 gm) in DMF (10 ml) was added slowly. Stirring was continued for one hour at room temperature and the solution was then evaporated under reduced pressure at 45° C. The resulting solid was suspended in methylene chloride, the insoluble inorganic solid was removed by filtration and the filtrate was evaporated to afford the title compound as a crystalline solid.

EXAMPLE 3

1-Benzyl-4-Hydroxy-6-Methyl-2(1H)-Quinolinone

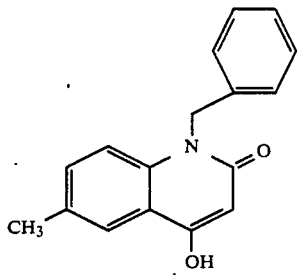

A solution of diethyl malonate (4.07 gm) in dimethyl acetamide (10 ml) was added dropwise to a stirred suspension of 60% sodium hydride (1.01 gm) in the same solvent (10 ml), under a nitrogen atmosphere, in an oil bath at 25° C. After hydrogen evolution ceased, the temperature was raised to 80° C. while adding a solution of 1-benzyl-6-methyl-isatoic anhydride (4.5 gm) in dimethyl acetal (DMA) (50 ml). After carbon dioxide evolution ceased, the reaction mixture was heated at 120° C. for 17 hours and then concentrated under reduced pressure to a volume of 25 ml. and diluted with water (50 ml). The milky solution was washed with ether, the aqueous layer was acidified with mineral acid to pH3 and the resulting crystalline product 1-benzyl-3-carbethoxy-6-methyl-2(1H)-quinolinone was added to 2N sodium hydroxide (150 ml). The mixture was refluxed for 4 hrs and the resulting solution was then cooled, acidified with mineral acid to pH3 and the solid was filtered, dried and crystallized from ethyl acetate/hexane to afford the title compound (4.0 gm). MS: m/e 265 (M).

PREPARATION B

EXAMPLE 4

1-Benzyl-4-Hydroxy-6-Chloro-2(1H)-Quinolinone

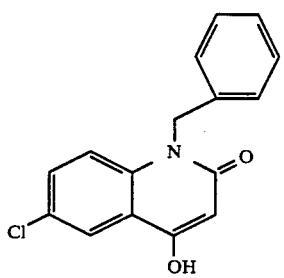

Obtained by starting with 2-amino-5-chloro-benzoic acid and using the procedure described in Preparation A. FAB MS: m/e 286 (M+1).

PREPARATION C

EXAMPLE 5

1-Benzyl-4-Hydroxy-7-Chloro-2(1H)-Quinolinone

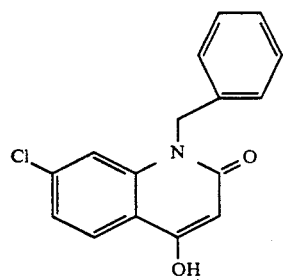

Obtained by starting with 2-amino-4-chloro-benzoic acid and using the procedure described in Preparation A. MS: m/e 285 (M).

PREPARATION D

EXAMPLE 6

1-Benzyl-4-Hydroxy-8-Methyl-2(1H)-Quinolinone

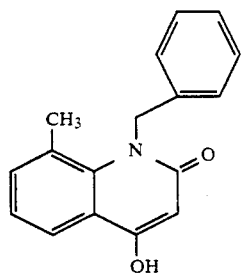

Obtained by starting with 2-amino-3-methyl-benzoic acid and using the procedure described in Preparation E

PREPARATION E

EXAMPLE 7

1-Hexyl-4-Hydroxy-6-Methyl-2(1H)-Quinolinone

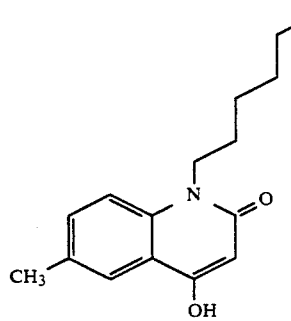

Obtained by using hexyl bromide in Example 2 of Preparation A. CI MS: m/e 260 (M+1).

PREPARATION F

EXAMPLE 8

1-Benzyl-4-Hydroxy-2(1H)-Quinolinone

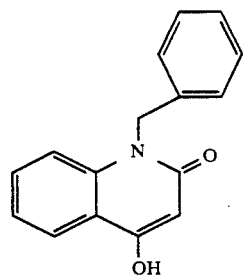

Obtained by starting with isatoic anhydride and following the procedure for Examples 2 and 3 of Preparation A. MS: m/e 251 (M).

PREPARATION G

Example 9

1-Hexyl-4-Hydroxy-2(1H)-Quinolinone

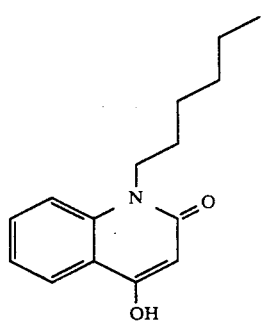

Obtained by using isatoic anhydride and hexyl bromide in Examples 2 and 3 of Preparation A. MS: m/e 245 (M).

PREPARATION H

EXAMPLE 10

1-Phenyl-4-Hydroxy-2(1H)-Quinolinone

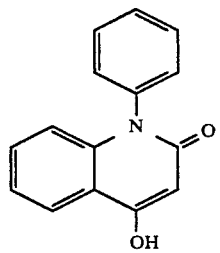

Obtained by starting with N-phenylamino benzoic acid and using the procedure in examples 1 and 3 of Preparation A. MS: m/e 237 (M).

PREPARATION I

EXAMPLE 11

1-[3-(2-Chloro-4-Methoxyphenoxy)propyloxymethyl]-4-Hydroxy-2(1H)-Quinolinone

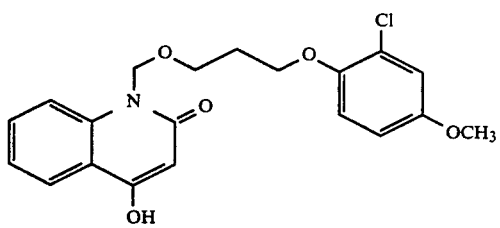

A solution of 2-chloro-4-methoxy-phenyl (15.5 gm) in DMF (20 ml) was added to a suspension of 60% sodium hydride (4 gm) in DMF (10 ml) followed by the addition of a solution of 3-chloropropyl benzoate (15.5 gm) in DMF (20 ml). The solution was heated at 80 for 20 hrs, diluted with ethyl acetate, washed with water dried and evaporated. The crude product was dissolved in a 1:1 mixture of methanol/THF (40 ml) to which 10% sodium hydroxide (50 ml) was added. The mixture was refluxed for 3 hours, diluted with ethyl acetate, washed with water and evaporated. The crude product was purified by chromatography on silica gel using 40% ethyl acetate in hexane as the eluting solvent and dissolved in dichloroethane (40 ml) containing paragormaldehyde (2.25 gm). The solution was cooled in an ice bath and a stream of HCl gas was bubbled through it for 3.5 hours, dried over magnesium sulfate and the resulting chloro-4-methoxyphenoxy) propyloxymethyl chloride and isatoic anhydride were reacted in a manner analogous to that set forth in Examples 2 and 3 of Preparation A to afford the title compound. MS: m/e 389 (m).

PREPARATION J

EXAMPLE 12

1-Benzyl-4-Hydroxy-6-Benzyloxy-2(1H)-Quinolinone

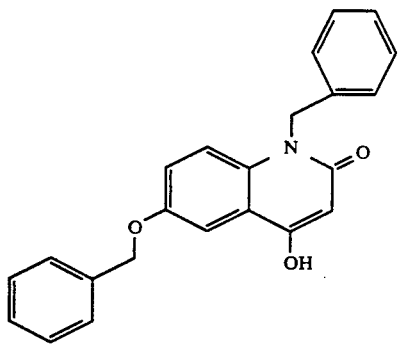

Obtained by starting with 2-amino-5-benzyloxy-benzoic acid and using the procedure described in Preparation A.

PREPARATION K

EXAMPLE 13

4-Benzyl-7-hydroxy-thieno[2,3-b]pyridine-5(4H)-one

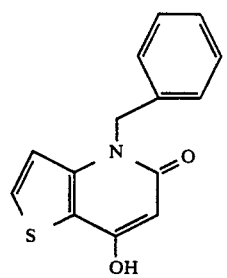

Obtained by starting with 3-amino-thiophene-2-carboxylic acid-benzoic acid and using the procedure described in Preparation A.

EXAMPLE 14

(E,Z) 1-Methyl-3-Benzylaminomethylene-Quinolin-2,4(1H)-Dione

Step 1

A suspension of 1-methyl-4-hydroxy-2(1H)-quinolinone (1.0 gm) in dimethyl formamide dimethyl acetal (5 ml) and methylene chloride (2.0 ml) was refluxed for 1 hour. The resulting dark orange solution was evaporated under reduced pressure to afford 1-methyl-3-dimethylaminomethylene-(1H)-quinolin-2,4-dione. MS: m/e 230 (M+).

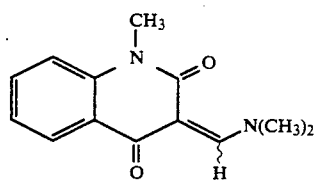

Step 2

The product from Step 1 was dissolved in methanol (20 ml) and dichloromethane (5 ml) followed by the addition of benzylamine (0.72 gm) in methanol (0.7 ml). The reaction mixture was stirred for 1 hour, diluted with ether ((50 ml) and filtered to afford the title compound (1.5 gm). MS: m/e 292 (M+).

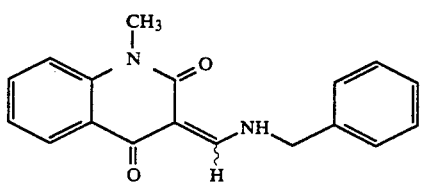

EXAMPLE 15

(E,Z)1-Benzyl-3-[4-Pyridylmethylamino)methylene]-6-Methyl-Quinolin-2,4(1H)-Dione

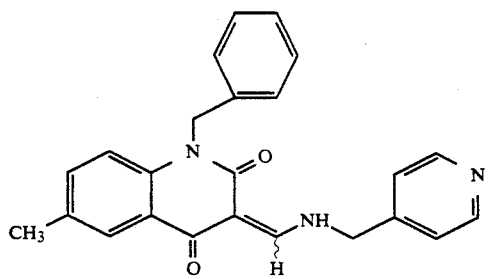

Obtained by starting with 1-benzyl-4-hydroxy-6-methyl-2(1H) quinolinone (Preparation A) and 4-aminomethylpyridine using the procedure described in Preparation B. MS m/e 383 (M).

EXAMPLE 16

(E,Z 1-Benzyl-3-Benzylaminomethylene-6-Chloro-Quinolin-2,4(1H)-Dione

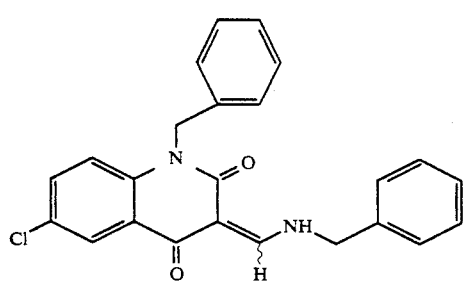

Obtained by starting with 1-benzyl-4-hydroxy-6-chloro-2(1H)-quinolinone (Example 4), and benzylamine using the procedure described in Preparation B. MS: m/e 402 (M).

EXAMPLE 17

(E,Z1-Benzyl-3-[(4-Pyridylmethylamino)methylene-6-Chloro-Quinolin-2,4(1H)-Dione

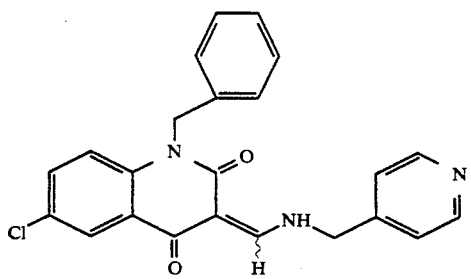

Obtained by starting with 1-benzyl-4-hydroxy-6-chloro-2(1H)-quinolinone (Example 1) and 4-aminomethylpridine using the procedure described in Preparation B. MS(FAB): m/e 404(M+1).

EXAMPLE 18

(E,Z)1-Benzyl-3-Benzylaminomethylene-7-Chloro-Quinolin-2,4(1H)-Dione

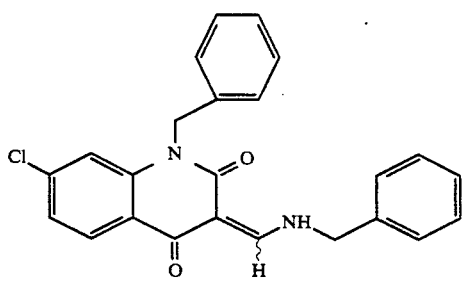

Obtained by starting with 1-benzyl-4-hydroxy-7-chloro-2(1)H)-quinolinone (Example 5) and benzylamine using the procedure described in Preparation B. MS: m/e 402 (M).

EXAMPLE 19

(E,Z)1-Benzyl-3-[(4-Pyridylmethylamino)methylene]7-Chloro-Quinolin-2,4(1H)-Dione

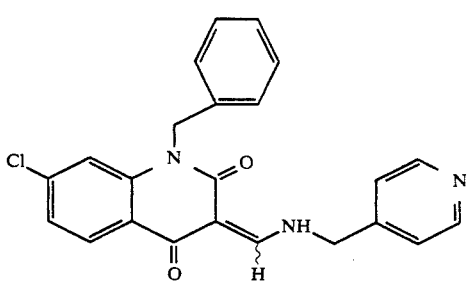

Obtained by starting with 1-benzyl-4-hydroxy-7-chloro-2(1H)-quinolinone (Example 5) and 4-aminomethylpyridine using the procedure described in Preparation B. MS: m/e 403 (M).

EXAMPLE 20

(E,Z) 1-Benzyl-3-Benzylaminomethylene-8-Methyl-Quinolin-2,4(1H)-Dione

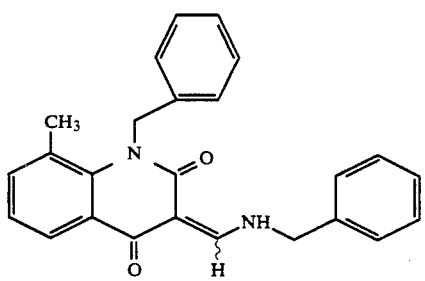

Obtained by starting with 1-benzyl-4-hydroxy-7-chloro-2(1H)-quinolinone (Example 6) and benzylamine using the procedure described in Preparation B. MS: m/e 382 (M).

EXAMPLE 21

(E,Z)1-Benzyl-3-[(4-Pyridylmethylamino)methylene]-8-Methyl-Quinolin-2,4(1H)-Dione

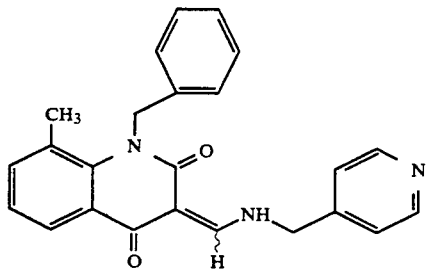

Obtained by starting with 1-benzyl-4-hydroxy-8-methyl-2(1H)-quinolinone (Example 6) and 4-aminomethylpyridine using the procedure described in Preparation B. MS: m/e 383(M).

EXAMPLE 22

(E,Z)1-Methyl-3-[(4-Pyridylmethylamino)methylene]-Quinolin-2,4(1H)-Dione

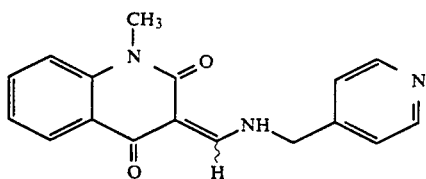

Obtained from 1-methyl-4-hydroxy-2(1H)quinolinone and 4-aminomethylpyridine using the procedure described in Preparation B. MS(FAB): m/e 294 (M+1);

EXAMPLE 23

(E,Z)1-Benzyl-3-Benzylaminomethylene-Quinolin-2,4(1H)-Dione

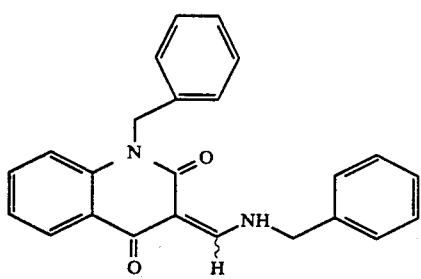

Obtained by starting with 1-benzyl-4-hydroxy-2(1H)-quinolinone (Example 8) and benzylamine using the procedure described in Preparation B. MS: m/e 374 (M).

EXAMPLE 24

(E,Z)1-Benzyl-3-[(4-Pyridylmethylamino)methylene]-Quinolin-2,4(1H)-Dione

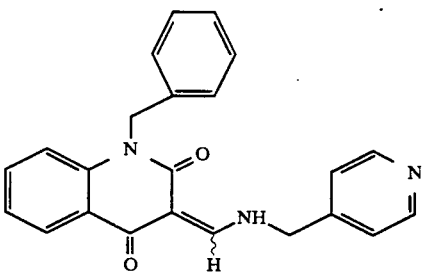

Obtained by starting with 1-benzyl-4-hydroxy-2(1H)-quinolinone (Example 8) and 4-aminomethylpyridine using the procedure described in Preparation B. MS: m/e 369 (M).

EXAMPLE 25

(E,Z)1-hexyl-3-benzyleminomethylene-quinolin-2,4(1H)-Dione

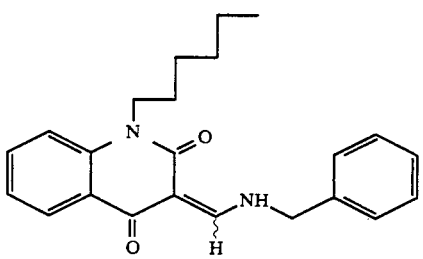

Obtained by starting with 1-hexyl-4-hydroxy-2(1H)-quinolinone (Example 9) and benzylamine using the procedure described in Preparation B. MS (Cl): m/e 383 (M+1).

EXAMPLE 26

(E,Z)1Hexyl-3-[(4-Pyrigylmethylamino)methylene-Quinolin-2,4(1H)-Dione

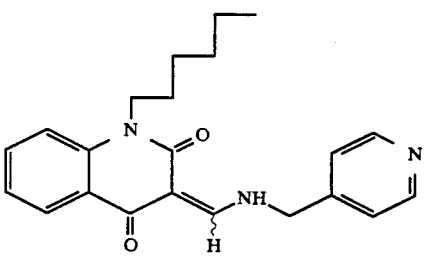

Obtained by starting with 1-hexyl-4-hydroxy-2(1H)-quinolinone (Example 9) and 4-aminomethylpyridine using the procedure described in Preparation B. MS(Cl): m/e 364 (M+1).

EXAMPLE 27

(E,Z)1-Phenyl-3-Benzylaminomethylene-Quinolin-2,4(1H)-Dione

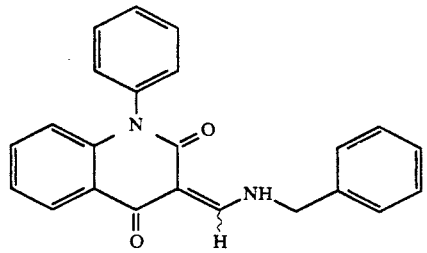

Obtained by starting with 1-phenyl-4-hydroxy-2(1H)-quinolinone (Example 10) and benzylamine using the procedure described in Preparation B. MS: m/e 354(M).

EXAMPLE 28

(E,Z)1-Phenyl-3-[(-Pyridylmethylamino)methylene]-Quinolin-2,4(1H)-Dione

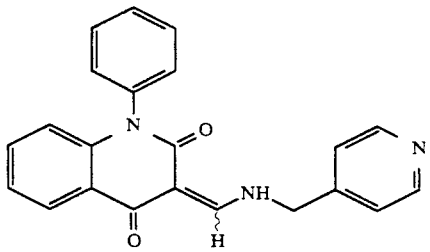

Obtained by starting with 1-phenyl-4-hydroxy-2(1H)-quinolinone (Example 10) and 4-aminomethylpyridine using the procedure described in Preparation B. MS: m/e 355 (M).

EXAMPLE 29

(E,Z)1-Heptyl-3-Benzylaminomethylene-Quinolin-2,4(1H)-Dione

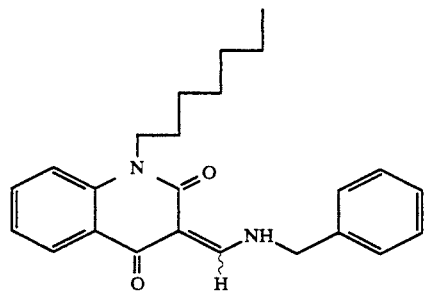

Obtained by starting with 1-heptyl-4-hydroxy-2(1H)-quinolinone and benzylamine using the procedure described in Preparation B. MS: m/e 376 (M).

EXAMPLE 30

(E,Z)-1-Heptyl-3-[(4-Pyridylmethylamino)methylene]-Quinolin-2,4(1H)-Dione

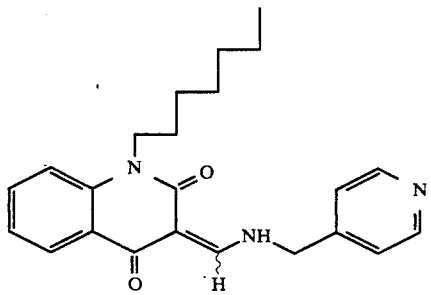

Obtained by starting with 1-heptyl-4-hydroxy-2(1)-quinolinone and 4-aminomethylpyridine using the procedure described in Preparation B. MS: m/e 377(M).

EXAMPLE 31

3-[1-Benzylaminoethylidine]-2,4-dioxo-2,3-dihydro-4H-pyrido-[2,3-b]-pyran

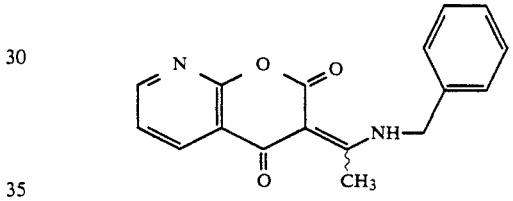

There was stirred for 20 hours at 25° a solution containing 2-chloronicotinoyl chloride (0.18 g), triethylamine (0.35 mL), ethyl 3-(benzylamino)-2-propenoate (0.25 g) and CH$_2$Cl$_2$ (10 mL). The major product was isolated by preparative TLC on silica gel with 3% acetone-CH$_2$Cl$_2$ and evaporated to obtain the intermediate as a brown oil (0.20 g).

The foregoing product (0.20 g) was refluxed with methanesulfonic acid (0.05 g) in 1,2-dichloroethane (10 mL) for 15 minutes, washed with aqueous sodium bicarbonate and the solution was filtered through a little silica gel, washing with 10% acetone-CH$_2$Cl$_2$. The product was evaporated and recrystallized from ether-hexanes to obtain the title compound (0.095 g) as a pale tan solid, mp 169°-171°.

EXAMPLE 32

1-Phenyl-3-(dimethylaminomethylene)-3,4-dihydro-2H-[1,8]-naphthyridine-2,4-dione

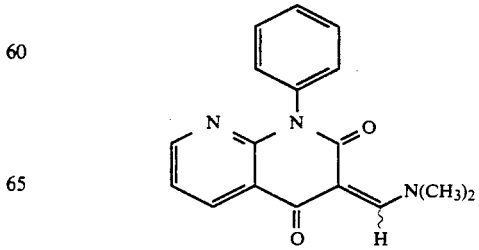

There was stirred for 5 hours at 25° a mixture of 1-phenyl-4-hydroxy-2H-3,4-dihydro-[1,8]-naphthyridine-2-one (6.75 g), the DMF-dimethylsulfate addict (10.0 g), ethyldiisopropylamine (15 ml) and dichloromethane (150 mL). The mixture was washed with 5% aqueous tartaric acid (2×200 mL), dried over Mg SO4 and evaporated. The solid was stirred with 10:1 ether-dichloromethane (100 mL) for 0,5 hours, filtered and dried to a yellowish-orange powder mp 215°–220° with decompositions, sufficiently pure for subsequent reactions.

EXAMPLE 33
3-(Dimethylaminomethylene)-dihydrobenzo[b]pyran-2,4-dione

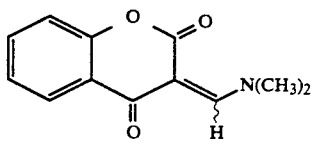

This compound was prepared by the method of example 2, by stirring 4-hydroxycoumarin (5.0 g) and DMF-dimethylsulfate (10.0 g) with ethyldiisopropylamine (10 mL) in CH2Cl2 (100 mL) for 0.5 hour. Product was crystallized from ether-CH2Cl2 to obtain 3.01 g of tan crystals, mp 135°–140° with decomposition.

EXAMPLE 34
E,Z-3-[Allylaminomethylene]-dihydrobenzo-[b]-pyran-2,4-dione

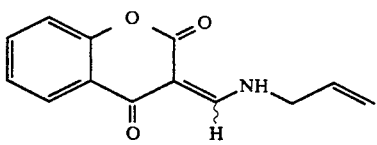

There was stirred a mixture of the compound of example 3 (1.0 g) and allylamine (0.6 mL) in CH2Cl2 (20 mL) for 10 minutes. The mixture was washed with aqueous tartaric acid, dried over MgSO4 and evaporated. The solid was triturated with ether to obtain the title compound as a mixture of E and Z isomers.

PMR (CDCl3): §4.2 (m,2), 5.3–5.5 (m,2), 5.9–6.1 (m,1), 7.2–8.2 (m,4), 8.45 (d, approx. 0.7), 8.60 (d. approx. 0.3) and 10.3 and 12.0 (both broad s, total 1).

EXAMPLE 35
1-Phenyl-E,Z-3-[ethylaminomethylene]-3,4-dihydro-2H-[1,8]-naphthyridine-2,4-dione

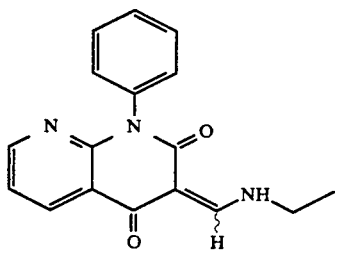

There was stirred for 10 minutes a solution of the dimethylamino compound (Example 32) (0.61 g) in CH2Cl2 (20 mL) with 70% aqueous ethylamine (0.5 mL). The mixture was washed with aqueous tartaric acid and aqueous sodium bicarbonate, dried, filtered and evaporated. The solid was triturated with ether and collected and dried to obtain the title compound as a solid (0.57 g) which is an approximately 3:2 mixture of the geometric isomers.

PMR (CDCl3): in addition to multiplets for the aromatic protons, the following are characteristic: §1.34 and 1.41 (both t, total=3), 3.5–3.7 (m,2), 11.05 and 12.10 (both br. s, total=1).

EXAMPLE 36
1-Phenyl-E,Z-3-[benzylaminomethylene]-3,4-dihydro-2H-[1,8]-naphthyridine-2,4-dione

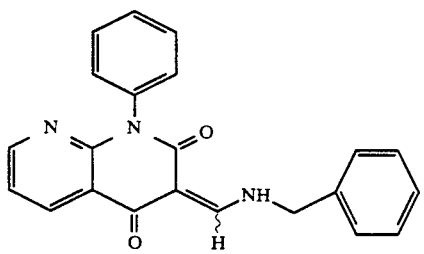

The title compound was prepared in a manner similar to Example 35, using 0.24 g of the dimethylamino compound and 0.1 g benzylamine in 10 mL CH2Cl2. The solid was worked-up and crystallized to obtain a white solid (0.28 g) which was a 1:1 E-Z mixture.

PMR (CDCl3): in addition to signals for aromatic protons, the sample shows: §4.67 and 4.71 (both d, total=2) and 11.3 and 12.5 (both br. s., total=1).

EXAMPLE 37
1-Phenyl-E,Z-3-[(6-methyl-2-pyridylamino)methylene]-3,4-dihydro-2H-[1,8]-naphthyridine-2,4-dione

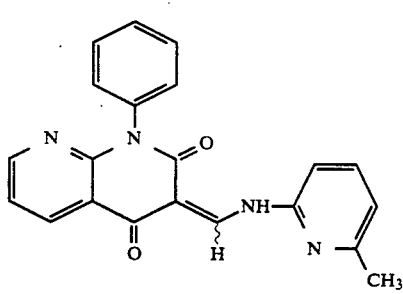

There was stirred a mixture in CH2Cl1 (20 mL) containing the dimethylamino compound (0.4 g) and 2-amino-6-methylpyridine (0.35 g) 25° for 20 hours then at 45° for 2 hours. The mixture was washed with aqueous tartoric acid, dried evaporated and chromatographed on silica gel with 5% acetone in CH2Cl2. The residue was crystallized by trituration with ether to obtain the title compound as a pale yellow solid (0.34 g) which was an approximately 1:1 E:2 mixture.

PMR (DMSO): 2.53 and 2.55 (both s, total=3), 7.1–8.5 (m,11), 9.50 and 9.59 (both d, total=1) and 12.54 and 13.43 (both br. d, total=1).

EXAMPLE 38

3-(ethylaminomethylene)-2,4-dioxo 3,4-dihydro-2H-pyrido-[2,3-b]-pyran

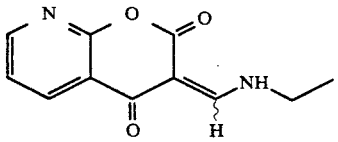

To a solution of 2,4-dioxo-3,4-dihydro-2H-pyrido-[2,3-b]-pyran (0.163 g) in dichloromethane (10 mL) was added diisopropylethylamine (0.35 mL) and the DMF-dimethylsulfate adduct (0.43 g) and the mixture was stirred for 20 hour at room temperature. There was added 70% ethylamine in water (0.5 mL). The mixture was stirred for 2 hours and worked up in dichloromethane-water, washed with aqueous tartoric acid, dried over magnesium sulfate and evaporated. The solid was triturated in ether containing a little dichloromethane collected and dried to give the product (0.10 g) is a white solid, mp 215°–217° (with decomposition) as an E/Z isomer mixture. 2,4-dioxo-3,4-dihydro-2H-pyrido-[2,3-b]-pyran is a known compound or may be prepared in accordance with known methods.

PMR (CDCl$_3$): §1.42 (t,3), 3.5–3.8(m,z), 7.25–7.4 (m,1), 8.35–8.6 (m,3), 10.35 and 11.7 (each broad s, total=1).

EXAMPLE 39

(E,Z)-1-heptyl-3-[(4-morpholino)aminomethylene]-quinolin-2,4(1H)dione

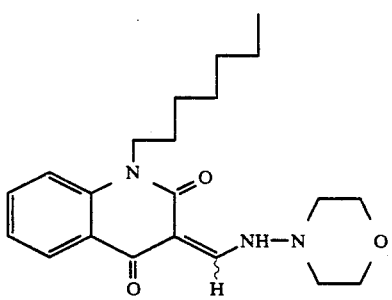

Obtained by starting with 1-heptyl-4-hydroxy-2(1H)-quinolone and 4-aminomorpholine and following the procedure described in Example 14. MS: m/e 371 (M+).

EXAMPLE 40

(E,Z)-1-heptyl-3-[1-adamantylaminomethylene]-quinolin-2,4(1H)dione

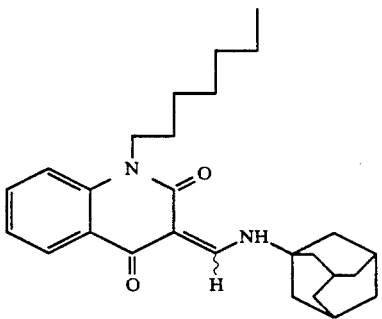

Obtained by starting with 1-heptyl-4-hydroxy-2(1H)-quinolone and 1-adamantylamine and following the procedure described in Example 14. MS:m/e 420 (M+).

EXAMPLE 41

(E,Z)-1-benzyl-3-[(1H-5-imidazolylmethyl)aminomethylene]-quinolin-2,4(1H)dione

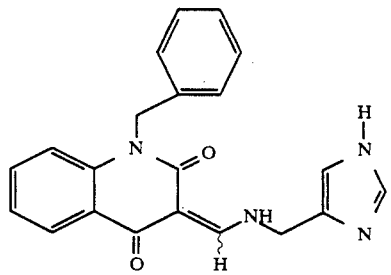

Obtained by starting with 1-benzyl-4-hydroxy-2(1H)-quinolone (Preparation of this compound is described in Example 8.) and 5-imidazolylmethylamine and following the procedure described in Example 14. MS:m/e 359 (M+1).

EXAMPLE 42

(E,Z)-1-hexyl-3-(D) glucosaminomethylene-quinolin-2,4(1H)dione

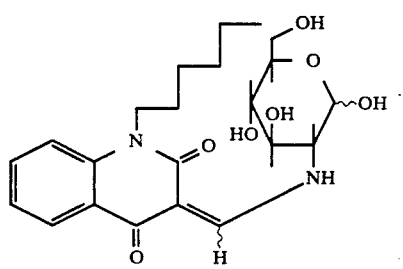

Obtained by starting with 1-hexyl-4-hydroxy-2(1H)-quinolone (Preparation of this compound is described in Example 9.) and D-glucosamine and following the procedure described in Example 14. MS(FAB): m/e 435 (M$^+$ +1).

EXAMPLE 43

(E,Z)
1-[3(2-chloro-4-methoxyphenoxy)-propyloxymethyl]-3-(4-pyridylmethylamino)methylene-quinolin-2,4(1H)dione

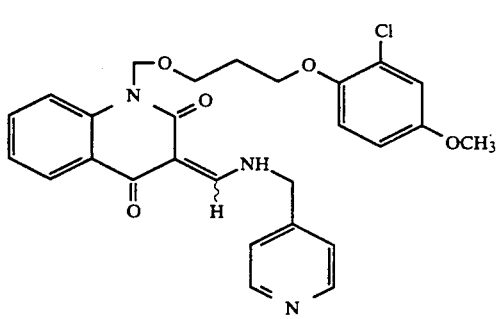

Obtained by starting with 1-[3-(2-chloro-4-methoxyphenoxy)-propyloxymethyl]-4-hydroxy-2(1H)-quinolinone (The making of this compound is described in Preparation I.) and 4-aminomethylpyridine and following the procedure described in Example 14. MS:m/e 508 (M+).

EXAMPLE 44

(E,Z)
1-methyl-3-ethylaminomethylene-quinolin-2,4(1H)dione

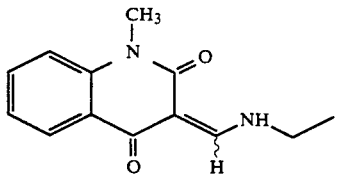

Obtained by starting with 1-methyl-4-hydroxy-2(1H)-quinolinone and ethylamine and following the procedure described in Example 14. MS:m/e 230 (M+).

EXAMPLE 45

(E,Z)
4-benzyl-6-benzylaminomethylene-thieno[3,2-b]pyridine-5,7(4H,6H)-dione

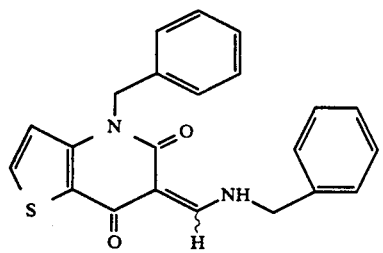

Obtained by starting with 4-benzyl-7-hydroxy-thieno[3,2-b]pyridine-5(4H)one (The making of this compound is described in preparation K.) and benzylamine and following the procedure described in Example 14. MS:m/e 374 (M+).

EXAMPLE 46

(E,Z)
4-benzyl-6-(4-pyridylaminomethylene-thieno[3,2-b]pyridine-5,7(4H,6H)-dione

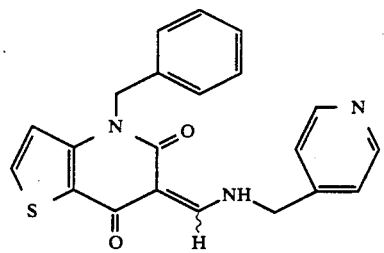

Obtained by starting with 4-benzyl-7-hydroxy-thieno[3,2-b]pyridine-5(4H)one (The making of this compound is described in preparation K.) and 4-aminomethylpyridine and following the procedure described in Example 14. MS: m/e 375 (M+).

BIOLOGICAL DATA

Cell and Virus Culture

HeLa and Vero cell cultures were maintained in Eagles Minimal Essential Medium (EMEM) which was supplemented with glutamine, penicillin, streptomycin and 10% fetal calf serum (10% EMEM). Stock cultures of HSV-2 (strain MS available from ATCC VR-540) were grown in and harvested from Vero cells. Viral stocks were titered in Vero cells according to established procedures.

Plasmid Constructions

Plasmid pON 245$^{ori-}$contains the promoter of the HSV-1 thymidine kinase (tk) gene located immediately 5' of the *E. coli* lac Z gene. In this arrangement, the tk promoter controls transcription from the bacterial gene in transient expression assays. Additionally, an SV40 polyadenylation signal is present at the 3' end of the lac Z gene to allow for the efficient translation of the mRNA in eucaryotic cells. The expression of beta galactosidase in a transient assay using pON 245$^{ori-}$ is dependent upon superinfection of the transfected cells with HSV. Therefore, a compound which interferes with early steps of HSV replication will also inhibit beta galactosidase production in transfected cells. For example see U.S. application Ser. No. 07/435,491 filed Sep. 5, 1989, the disclosure of which is incorporated herein by reference thereto.

Transient Expression of Beta Galactosidase in Transfected Cells

HeLa cells were seeded into 96 well microtiter plates and allowed to grow to 80% confluency (approximately 35,000 cells/well). One half microgram of plasmid pON 245$^{ori-}$ DNA was introduced into the cells of each well by the DEAE Dextran precipitation technique (Grahman and Van der Eb, 1973). Four to six hours later, the cells were rinsed with hank's Balanced Salt Solution (HBSS), overlaid with 10% EMEM and incubated at 37° C. At 24 hrs post-transfection, cells were rinsed, overlaid with 10% EMEM again and reincubated at 37° C. At 48 hrs post-transfection, cells were rinsed and overlaid with either EMEM containing 2% fetal calf serum (2% EMEM), 2% EMEM containing HSV-2 (strain MS, Multiplicity of Infection [moi]=5 pfu/cell) or 2% EMEM containing HSV-2 and the appropriate concentration of Schering compound to be tested. Twenty-four hours later, the cells were harvested and assayed for beta galactosidase activity as described below.

Beta Galactosidase Assay

All determinations of beta galactosidase activity were performed in 96 well microtiter plates. The intracellular level of beta galactosidase activity in each well was determined from cell lysates of the monolayer cultures. Aliquots were assayed by incubation in the presence of beta galactosidase substrate, 4-methylumbelliferyl-$\beta$-D-galactoside (MUG, 125 ug/ml, Sigma), for 2 hours. The generation of fluorescent product was quantified on a Microfluor microfluorimeter (Dynatech) after addition of 0.1M glycine, pH 10.3 (Spaete and Mocarski, 1985). The inhibitory activity of a compound was plotted versus the concentration and an IC50 value (the concentration of compound required to reduce beta glactosidase expression by 50%) was obtained for each compound tested.

Compound Toxicity Assay

Compounds which demonstrated a significant inhibitory activity in the HeLa cell beta galactosidase assay were assayed for their inhibitory effect on HeLa cell translation. HeLa cells were treated with inhibitory compound for 24 hours, after which levels of translational activity were assayed.

For assay of translational activity, HeLa cultures were grown to 80% confluency in 96 well microtiter plates, treated with appropriate concentrations of compound in 2% EMEM during an overnight incubation at 37° C., then rinsed with HBSS and overlaid with 0.8 ml of 2% EMEM containing 8 uCi of tritiated leucine ($^3$H-LEU, 141 Ci/mMol, Amersham Corp., Arlington Heights Ill.). After 1 hr incubation at 36.5° C., the cells were rinsed twice with phosphate buffered saline (PBS) and lysed in 400 ul/well of 1×PBS, 0.5% sodium dodecyl sulphate (SDS). After a 10 minute incubation at 36.5° C., the contents of the well were transferred to a well in a Millititer HA microfiltration plate (Millipore Corp., Bedford, MA). The TCA insoluble proteins were precipitated onto the filter disc by a 10 minute fixation with 5% TCA, followed by filtration under vacuum and three 10 minute rinses with 95% ethanol. The filters were dried at room temperature, cut from the milltitier plate and transferred to scintillation vials. TCA precipitable counts were assayed in 5 ml of Scintisol (Isolab, Akron, Ohio). The inhibitory activity of a compound was plotted versus the concentration and an IC$_{50}$ value (that concentration of the compound required to decrease cellular translational activity by 50%) was derived for each compound.

Analysis of In Vivo Efficacy

The in vivo assessment of anti-HSV efficacy was determined in the prophylactic guinea pig model of HSV infection described by Stanberry et al (1982) The Journal of Infectious Diseases-vol. 146, No. 3, pages 397–404, which is hereby incorporated by reference. Dosing of guinea pigs was comprised of an initial treatment with test compound given 24 hours prior to virus infection and subsequent administration of the compound every eight hours (T.I.D.) for a total of 10 days. Test compounds were administered subcutaneously in 0.5% buffered methyl cellulose at a dose of 60 mg per kg body weight of the animal. Animals were monitored daily for the development of genital lesions and neurological symptomology, both of which were recorded and compared to the results obtained with parallel groups which received placebo or acyclovir treatment. Efficacy was evaluated for each compound by scoring the ability of the compound to ameliorate genital lesions produced by infection with HSV-2, strain MS, expressed as Activity Coefficients. The Activity Coefficients. were calculated as follows: The ability of a test compound to ameliorate lesions was plotted graphically with the number of days being on one axis, and the number of lesions being on the other axis. The area under the resultant curve was put in the numerator of a fraction with the denominator either being the area under a similar curve where placebo was employed (EXP/PL), or the area under the curve where acyclovir was employed (EXP/ACV). Thus (Exp/PL) is the ratio of test compound to placebo. (Exp/ACV) is the ratio of test compound to acyclovir. The smaller the number obtained, the more effective was the compound tested.

In the therapeutic guinea pig model, dosing of guinea pigs started 24 hours after they were infected with the virus. Subsequent administration of the test compound was done every eight hours for a total of ten days. Activity coefficients were calculated in the same manner as described for the prophylactic guinea pig model above.

IN-VITRO ANTI-HSV ACTIVITY

The in-vitro anti-HSV activity of compounds of the invention is set forth in Table I.

TABLE I

| COMPOUND (The Example in which the compound appears is given.) | ANTI-HSV ACTIVITY HSV-$\beta$-GAL ASSAY IC$_{50}$($\mu$g/ml) | CYTOTOXICITY $^3$H—LEU ASSAY IC$_{50}$ ($\mu$g/ml) |
|---|---|---|
| EX. 31 | 11 | >100 |
| EX. 32 | 18 | >100 |
| EX. 35 | 7 | >50 |
| EX. 34 | 8 | 46 |
| EX. 36 | 22 | 42 |
| EX. 37 | 22 | 56 |
| EX. 38 | >25 | |
| EX. 15 | 6 | 37 |
| EX. 16 | 3< | 7 |
| EX. 17 | 4 | 17 |
| EX. 18 | 6 | 10 |
| EX. 19 | 13 | 40 |
| EX. 20 | 3 | 10 |
| EX. 21 | 3< | 29 |
| EX. 22 | 3< | 100 |
| EX. 23 | 5 | 100> |
| EX. 24 | 10 | 100> |
| EX. 25 | 3< | 37 |
| EX. 26 | 4 | 43 |
| EX. 27 | 4 | 10 |
| EX. 28 | 7 | 25 |
| EX. 29 | 5 | 16 |
| EX. 30 | 3 | 20 |
| EX. 39 | 4 | 29 |
| EX. 40 | 5 | 33 |
| EX. 41 | 8 | 34 |
| EX. 42 | 10 | 25 |
| EX. 43 | 10 | 30 |
| EX. 44 | 14 | 43 |
| EX. 45 | 4 | 40 |
| EX. 46 | 3 | 23 |
| EX. 14 | 9 | 27 |

IN-VIVO ANTI-HSV ACTIVITY

The in-vivo anti-HSV activities of compounds of this invention are set forth in Table II.

TABLE II

| COMPOUND (EXAMPLE) | Regimen | Activity Coefficients[1] | |
|---|---|---|---|
| | | (Exp/PL) | (Exp/ACV) |
| 23 | 60 mpk × 3/24 hr (sc, pro) | 0.67 ± 0.03 | 4.05 ± 2.21 |
| 45 | 30 mpk × 3/24 hr (sc, ther) | 0.71 | 0.93[2] |

[1]Activity Coefficients represent the ratio of the test compound (EXP) to placebo (PL) and to ACV (acyclovir) groups, respectively, as was determined for area under curve (AUC) calculations for lesions scores from days 1–10.
[2]ACV was not efficaceous in this study. mpk means milligrams per kilogram body weight. sc means subcutaneous. pro means prophylactic. ther means therapeutic.

The invention being thus described, it will be obvious that the same may be varied in many ways. Such variations are not to be regarded as a departure from the spirit and scope of the invention and all such modifications are intended to be included within the scope of the claims.

What is claimed is:

1. A compound of the formula

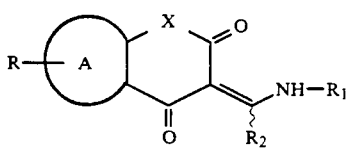

I or a pharmaceutically acceptable salt thereof wherein,
R is H, halogen, (C$_1$–C$_6$) alkyl, N(C$_1$–C$_6$ alkyl)$_2$, OH, O—(C$_1$–C$_6$) alkyl, CH$_2$OH, COOH, COO-alkyl, SO$_2$NH$_2$ or SO$_2$NH (C$_1$–C$_6$ alkyl);
R$_1$ is C$_1$–C$_6$ alkyl,

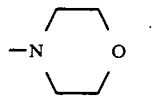

adamantyl, C$_2$–C$_6$ alkenyl, —CH$_2$-phenyl, —CH$_2$-pyridyl

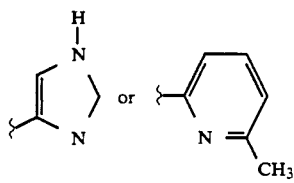

R$_2$ is H, or C$_1$–C$_6$ alkyl;

is phenyl, or
X is N-C$_1$–C$_8$ alkyl or phenyl (C$_1$–C$_6$) alkyl or

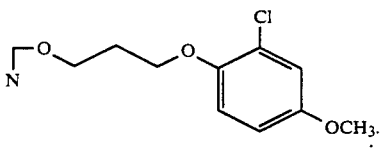

2. A compound according to claim 1 wherein X is selected from the group consisting of N-benzyl, N-hexyl, and N-heptyl.
3. A compound according to claim 1, wherein

is phenyl.
4. A compound according to claim 1 wherein R$_2$ is H.
5. A compound according to claim 1 wherein R$_1$ is selected from the group consisting of benzyl and —CH$_2$-pyridyl.
6. A compound according to claim 1 wherein R is H, halogen, or C$_1$–C$_6$ alkyl.
7. A compound according to claim 1 wherein

is an aromatic ring, R is H, Cl, or methyl, R$_2$ is H, and R$_1$ is benzyl or —CH$_2$-pyridyl. pyridyl.
8. A compound, selected from the group consisting of:

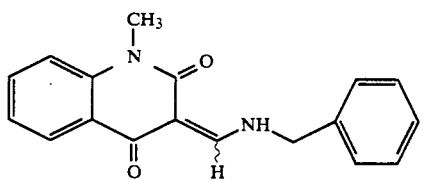

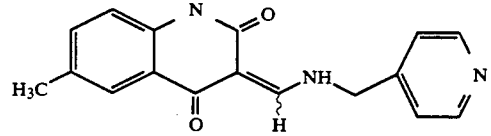

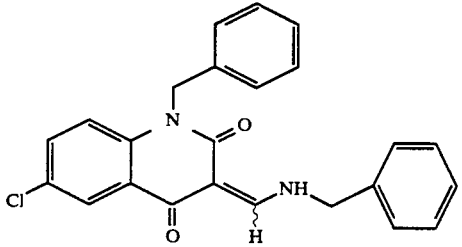

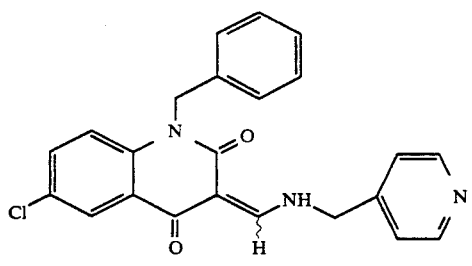
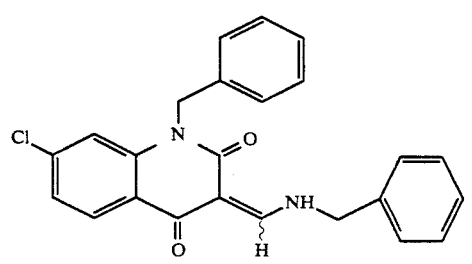
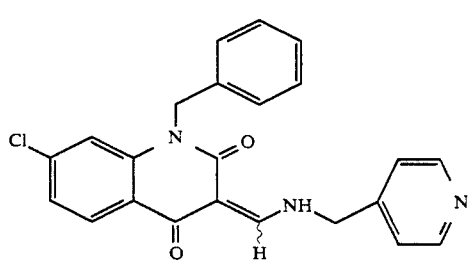
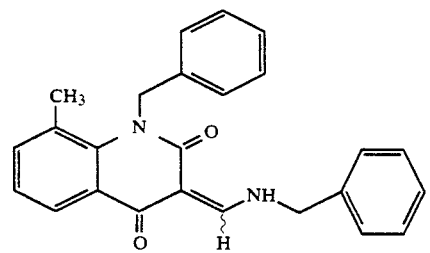
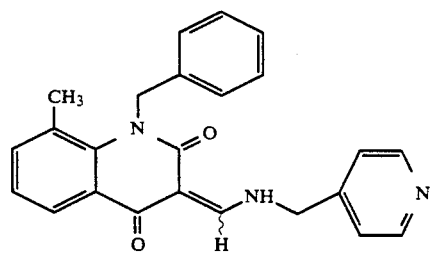
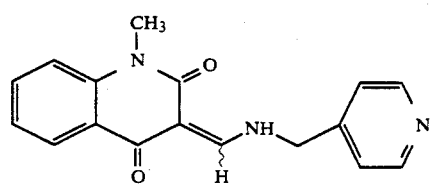
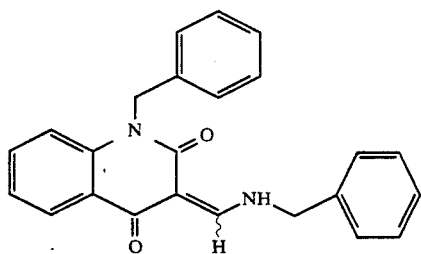
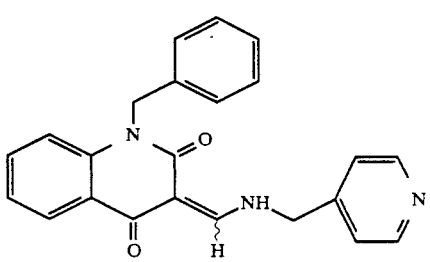
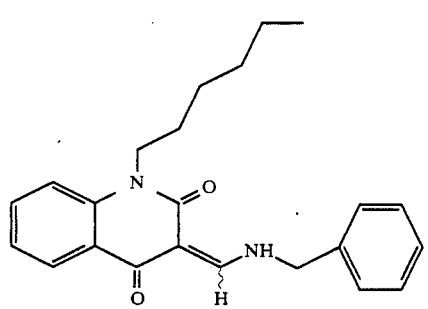
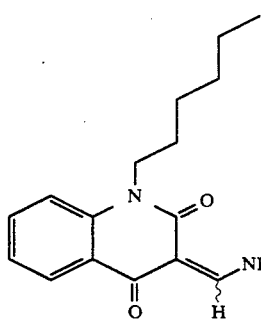
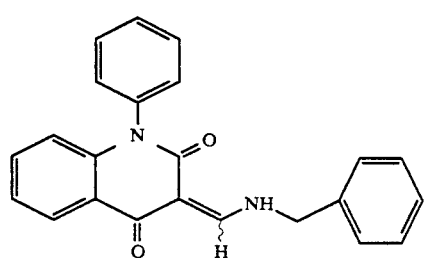

-continued

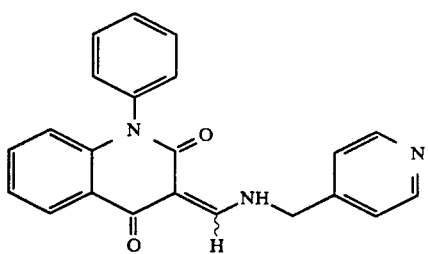

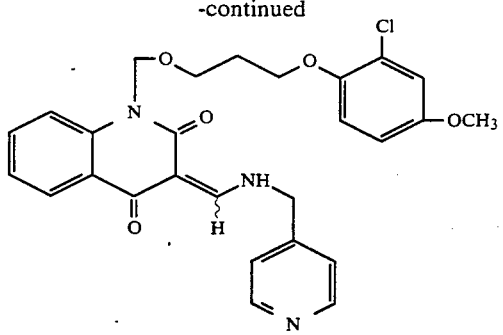

or a pharmaceutically acceptable salt thereof.
9. A compound according to claim 8, selected from the group consisting of:

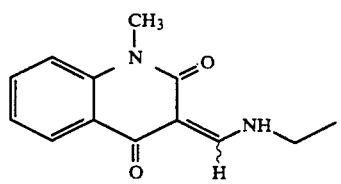

or a pharmaceutically acceptable salt thereof.
10. A compound;

or a pharmaceutically acceptable salt thereof.
11. A pharmaceutical composition comprising an anti-herpes group virus effective amount of a compound as defined in claim 1 in combination with a pharmaceutically acceptable carrier.
12. A method for treating anti-herpes group viral infections in a mammal which comprises administering to a mammal in need of such treatment an anti-herpes group virally effective amount of a compound according to claim 1.

* * * * *